United States Patent
Huang et al.

(10) Patent No.: US 12,221,602 B2
(45) Date of Patent: Feb. 11, 2025

(54) PREDICTING BIOREACTOR PRODUCT PRODUCTION BASED ON INDEPENDENT OR MULTIVARIATE ANALYSIS OF MULTIPLE PHYSICAL ATTRIBUTES

(71) Applicant: CENTRE FOR COMMERCIALIZATION OF REGENERATIVE MEDICINE, Toronto (CA)

(72) Inventors: Shuohao Huang, Toronto (CA); Gary Pigeau, Burglington (CA); Azher Razvi, Etobicoke (CA)

(73) Assignee: CENTRE FOR COMMERCIALIZATION OF REGENERATIVE MEDICINE, Toronto (CA)

( * ) Notice: Subject to any disclaimer, the term of this patent is extended or adjusted under 35 U.S.C. 154(b) by 996 days.

(21) Appl. No.: 17/051,925

(22) PCT Filed: Apr. 30, 2019

(86) PCT No.: PCT/CA2019/050558
§ 371 (c)(1),
(2) Date: Oct. 30, 2020

(87) PCT Pub. No.: WO2019/210405
PCT Pub. Date: Nov. 7, 2019

(65) Prior Publication Data
US 2021/0115383 A1     Apr. 22, 2021

Related U.S. Application Data

(60) Provisional application No. 62/665,155, filed on May 1, 2018.

(51) Int. Cl.
*C12M 1/36* (2006.01)
*G16C 20/70* (2019.01)

(52) U.S. Cl.
CPC .............. *C12M 41/48* (2013.01); *G16C 20/70* (2019.02)

(58) Field of Classification Search
CPC ...... C12M 41/48; C12M 41/26; C12M 41/32; C12M 41/34; C12M 41/36; C12M 41/42; G16C 20/70
See application file for complete search history.

(56) References Cited

U.S. PATENT DOCUMENTS 8,233,959 B2 * 7/2012 Kamath ............... A61B 5/1495
600/347
2009/0104594 A1 * 4/2009 Webb ..................... C12M 41/48
435/286.7

(Continued)

FOREIGN PATENT DOCUMENTS

| EP | 0156176 A1 | 10/1985 |
| EP | 0661380 A2 | 7/1995 |
| EP | 1851303 B1 | 11/2017 |

OTHER PUBLICATIONS

PCT International Search Report and Written Opinion, PCT/CA2019/050558, Jul. 15, 2019, 10 pages.

(Continued)

*Primary Examiner* — Lydia Edwards
(74) *Attorney, Agent, or Firm* — Smart & Biggar LP; Carmela De Luca

(57) ABSTRACT

In an aspect, there is provided a computer-implemented method for approximating product production in a bioreactor. The method comprises: providing a bioreactor containing live cells in a substrate, the bioreactor for cultivating, over a time period, a product derived from or of the cells during a manufacturing process; providing two or more sensors for measuring respective two or more different physical attributes of the substrate during the time period; receiving, at a processor, sensor data from the two or more (Continued)

sensors; and determining via the processor, based on a predetermined or recursive algorithm that correlates the sensor data and the product production by independent consideration of the sensor data of the two or more different physical attributes or by multivariate consideration of the sensor data of the two or more different physical attributes, an approximate amount of the product.

13 Claims, 10 Drawing Sheets

(56) References Cited

U.S. PATENT DOCUMENTS

| | | | |
|---|---|---|---|
| 2012/0107921 A1* | 5/2012 | Willson | C12M 41/48 47/1.4 |
| 2016/0145563 A1 | 5/2016 | Berteau et al. | |
| 2018/0010082 A1 | 1/2018 | Jaques et al. | |

OTHER PUBLICATIONS

Extended European Search Report dated Aug. 12, 2021 issued for related EP Application No. 19796844.9.

* cited by examiner

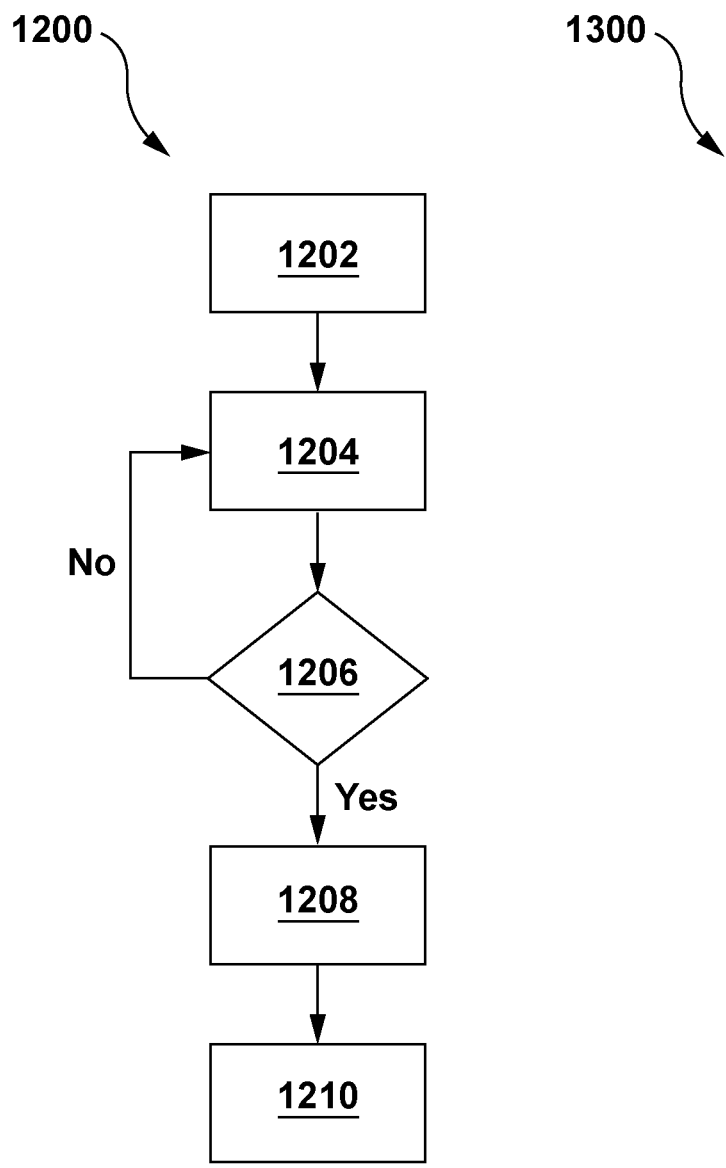
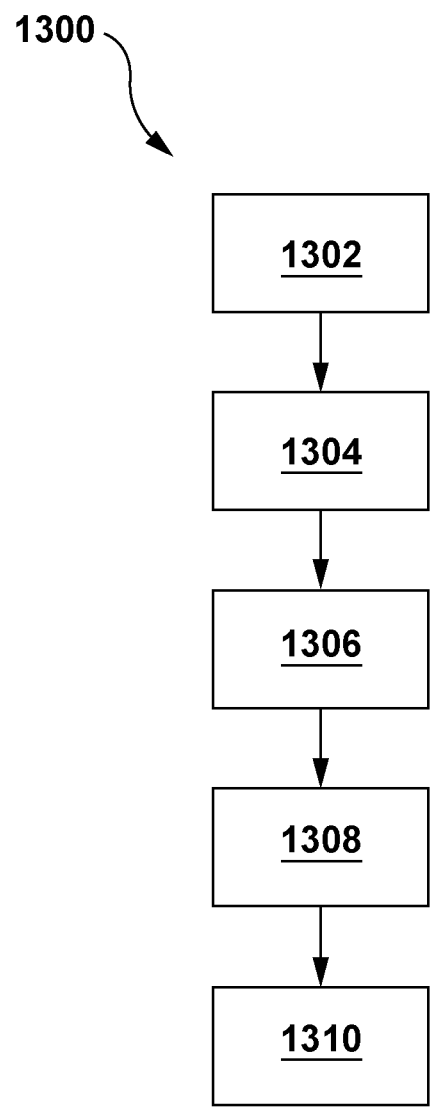
FIG. 12
FIG. 13

PREDICTING BIOREACTOR PRODUCT PRODUCTION BASED ON INDEPENDENT OR MULTIVARIATE ANALYSIS OF MULTIPLE PHYSICAL ATTRIBUTES

CROSS REFERENCE TO PRIOR APPLICATIONS

This application represents the national stage entry of PCT International Application No. PCT/CA2019/050558, filed Apr. 30 2019, which claims the benefit of priority to U.S. provisional patent application No. 62/665,155, filed May 1, 2018, and entitled "PREDICTING BIOREACTOR PRODUCT PRODUCTION BASED ON INDEPENDENT OR MULTIVARIATE ANALYSIS OF MULTIPLE PHYSICAL ATTRIBUTES" both the content of which are incorporated herein by reference in their entirety.

FIELD OF THE DESCRIPTION

The present description relates to manufacturing processes of therapeutic cell technologies in bioreactors. In particular, the present description relates to a multivariate predictive model of viable cell biomass.

BACKGROUND OF THE DESCRIPTION

Bioreactors have a long history in the cultivation of cells and cell products. In its simplest form, a bioreactor is a container with living cells and substrate, which are converted to product over time. The product may be intra- or extra-cellular, or in the case of therapeutic cell technologies, may be the cells themselves. Bioreactors may include sensor technology, designed to measure single or multiple conditions within the media substrate. Traditionally, these measured conditions may include (but are not limited to): temperature, pH, dissolved oxygen (DO), reduction-oxidation (redox) potential, agitation, gas flows (in and out), pressure, and vessel weight. Advancements in sensor technology have expanded the range of analytics possible to include (but not limited to): NIR, FTIR, Raman, optical, immobilized enzyme-linked metabolite measures, radar, conductivity, refractometry, and the like.

The cultivation of therapeutic cell technologies in fully-closed, process-controlled bioreactors is a new manufacturing endeavor, with only two autologous products on the market as of 2017: Novartis, Kymriah and Gilead, Yescarta. However, there are numerous candidates in development. The choice and use of various sensor technologies in a manufacturing bioreactor platform will vary depending on cost, reproducibility, dependability, ease of use, and safety.

With existing bioreactor systems, a physically invasive procedure is employed to determine whether cell biomass production is increasing or otherwise in line with expectations: authorized laboratory personnel are required to put on appropriate protective gear (which may comprise gloves and gowns or full-containment body suits, for example), extract from the bioreactor one or more aliquots of the media substrate, and thereafter analyze the substrate contents to determine cell count, among other variables. This method of determining cell biomass production has certain drawbacks, including: 1) the removal of aliquots of media substrate amounts to the removal of cells that otherwise may have been available for therapeutic application; 2) the physical removal of samples introduces the risk of contamination (which could result in the destruction of the batch, loss of upwards of hundreds of thousands, or even millions, of dollars, and the loss of life); 3) the requirement for personnel and equipment to physically obtain samples has an associated time and monetary cost; and 4) due to the above-noted disadvantages, the number of sampling events are restricted, often to once or twice per day, providing limited information on the state of the cell culture and not enabling efficient corrective actions to be taken. For example, autologous cell therapies require patient-specific starting material and are created to administer only to the donor. A contamination event and/or a reduction in number of viable therapeutic cells through sample withdrawal would place the patient at risk as the starting material and product output are in very limited, singular supply. Allogeneic cell therapies are not patient specific and as such, represent an opportunity for scale-up manufacturing of multiple doses in a single manufacturing run. Larger volumes and the associated materials costs represent a significant risk of loss to the manufacturer experiencing a sample withdrawal-based contamination event. From the (10's to 1000's of) patients' perspective, the risk of a contaminated production run would range from a delay in receiving a curative cell therapy to a catastrophic loss of life through administration of compromised cellular material.

It is desirable to obviate or mitigate one or more of the above deficiencies.

SUMMARY OF THE DESCRIPTION

The presently described embodiments comprise the combination of sensor-based data of a bioreactor in order to control aspects of the manufacturing process, as well as predict the density of viable cells and cell products. The predicted viable cells and cell product densities or amounts are produced by leveraging the combined relationships between multiple continuous process variables comprising physical attributes. These predictions of growth based on measurements of multiple physical attributes are then used to inform process decisions (for example, increasing feed, gas or agitation rates).

The presently described embodiments are expected to provide a more robust prediction through the use of multiple physical attribute sensor readings, allowing for redundant coverage in case of sensor failure or abnormalities and/or improved prediction based on multiple sensor inputs.

The presently described embodiments tend to allow for sample-free manufacturing of cells and cell products, thereby reducing contamination risks and product loss from sample withdrawal.

In a first aspect, there is provided a computer-implemented method for approximating product production in a bioreactor. The method comprises: providing a bioreactor containing live cells in a substrate, the bioreactor for cultivating, over a time period, a product derived from or of the cells during a manufacturing process; providing two or more sensors for measuring respective two or more different physical attributes of the substrate during the time period; receiving, at a processor, sensor data from the two or more sensors; and determining via the processor, based on a predetermined or recursive algorithm that correlates the sensor data and the product production by independent consideration of the sensor data of the two or more different physical attributes or by multivariate consideration of the sensor data of the two or more different physical attributes, an approximate amount of the product. In a further aspect, there is provided a method of determining a rate of supply of a process input to the bioreactor. The method comprises: providing a target product density; determining the approximate amount of the product via the above computer-implemented method for approximating product production in the bioreactor; comparing, via the processor, the approximate amount of the product to the target product density; determining via the processor, based on the comparing, the rate of supply of the process input to the bioreactor required to achieve the target product density within the time period; and adjusting the rate of supply of the process input to the bioreactor to the determined rate of supply of the process input.

In another aspect, there is provided a system for approximating product production in a bioreactor. The system comprises: a bioreactor for cultivating, over a time period, a product derived from or of live cells in a substrate during a manufacturing process; two or more sensors for measuring respective two or more different physical attributes of the substrate during the time period; a computing device communicatively coupled to the two or more sensors. The computing device comprises: a processor; a memory; and a communication module. The processor is communicatively coupled to the memory and the communication module, and is configured to: receive sensor data from the two or more sensors; and determine, based on a predetermined or recursive algorithm stored in the memory that correlates the sensor data and the product production by independent consideration of the sensor data of the two or more different physical attributes or by multivariate consideration of the sensor data of the two or more different physical attributes, an approximate amount of the product. In a further aspect, there is provided a system for determining a rate of supply of a process input to the bioreactor. The system comprises the above described system for determining the approximate amount of the product, and: a feedback controller communicatively coupled to the computing device and the bioreactor, wherein the processor is further configured to: compare the approximate amount of the product to a target product density; determine, based on the comparison, the rate of supply of the process input to the bioreactor required to achieve the target product density within the time period; and communicate to the feedback controller, via the communication module, an adjusted rate of supply of the process input to the bioreactor. Upon receipt, from the communication module of the computing device, of the adjusted rate of supply of the process input, the feedback controller adjusts the rate of supply of the process input to the bioreactor to the rate of supply of the process input determined by the processor.

In yet a further aspect, there is provided a non-transitory computer readable medium comprising computer-executable instructions for approximating product production in a bioreactor, the bioreactor for cultivating, over a time period, a product derived from or of live cells in a substrate during a manufacturing process, the bioreactor comprising two or more sensors for measuring respective two or more different physical attributes of the substrate during the time period. The computer-executable instructions when executed cause a processor to: determine, based on a predetermined or recursive algorithm that correlates sensor data received from the two or more sensors and the product production by independent consideration of the sensor data of the two or more different physical attributes or by multivariate consideration of the sensor data of the two or more different physical attributes, an approximate amount of the product.

BRIEF DESCRIPTION OF THE DRAWINGS

Example embodiments will now be described with reference to the appended drawings in which:

FIG. 12 depicts a flow diagram of another example embodiment of computer executable instructions described herein;

FIG. 13 depicts a flow diagram of yet another example embodiment of computer executable instructions described herein.

DETAILED DESCRIPTION OF NON-LIMITING EXAMPLE EMBODIMENTS

Figure 1:
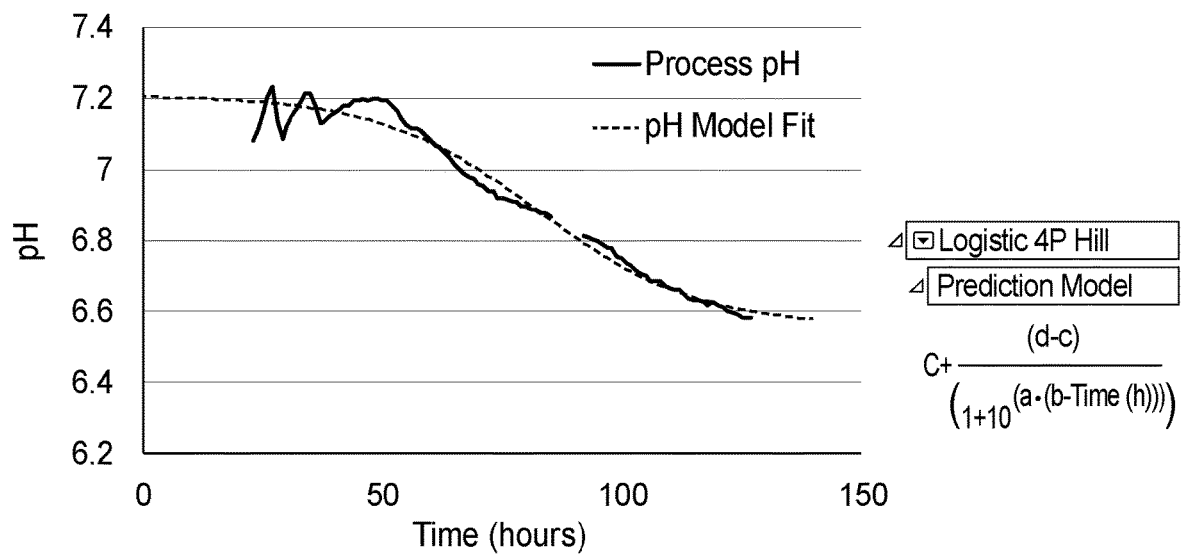
FIG. 1 depicts an example of a prediction model (right) and process data with model fit (left) for pH vs. time in a 10 L pluripotent stem cell bioreactor expansion.

Unless defined otherwise, all technical and scientific terms used herein generally have the same meaning as commonly understood by one of ordinary skill in the art to which this invention pertains.

The presently described embodiments are expected to provide for dynamic process control and product harvest timing in a sample-free manner. Expected advantages of enabling sample-free manufacturing of therapeutic cell technologies include reduced contamination risk and an increase in the number of cells available for the subsequent therapeutic dose, which benefit both the manufacturer and the end-patient. The presently described embodiments contemplate the use of inline sensor technology to build a multivariate model to predict viable cell concentration and allow for dynamic process control and product harvest timing. In this manner, the presently described embodiments are expected to overcome the limitations of single input single output control loops, by combining data streams from multiple sources to predict a single output. Through the use of multiple inputs, the presently described embodiments are expected to result in a more robust predictive algorithm, which is able to withstand perturbations to the system and contributing data streams while continually predicting an accurate, or close approximation of, concentration of cells or cellular product(s) or related measurements.

Allogeneic Example—Pluripotent Stem Cell Manufacturing

In the manufacture of allogeneic pluripotent stem cells (PSCs), a bioreactor may be used to scale production to manufacture a large batch with multiple doses. To reach clinically relevant cell production, a seed train of process-controlled stirred tank bioreactors may be used. In this example, correlations between pH and DO are demonstrated to predict viable cell density and provide information required in order to adaptively adjust media feed rate and predict the harvest time required for passage to the next vessel in the seed train.

As the expansion of PSCs proceeds, waste products such as lactic acid accumulate and nutrients/thermal labile components such as growth factors decline. Media feeding solutions are often applied to counteract these phenomena and are often increased in rate in response to cellular growth and/or metabolite accumulation/depletion. Regardless of the variable driving the decision, traditionally feed rates are adjusted in response to some sample-based data. The inventors have found that previous process development runs with sampling had established optimal cell densities at which to increase feed rates, and developed correlations between pH and DO to viable cell density which allow for adjustment of the feed rate without sample withdrawal.

The process correlations were developed through fitting the continuous process data with an appropriate function. In one example, the data was well fit (r2=0.976) to a logistic 4 parameter Hill function, but the skilled person in the art would appreciate that there are many other models that could be utilized. Equation and fit to the raw data are shown in FIG. 1, which depicts an example of a prediction model (right) and process data with model fit (left) for pH vs time in a 10 L pluripotent stem cell bioreactor expansion.

In another manufacturing run, samples were withdrawn and cell counts were performed. This allowed for the generation of a fitted growth curve. In this case a Gompertz 3 parameter equation was well fit (r2=0.991), but the skilled person in the art would appreciate that there are many other models that could be used. Equation and fit to the raw data are shown in FIG. 2, which depicts an example of a prediction model (right) and sample-based data with model fit (left) for cell count vs time in a 10 L pluripotent stem cell bioreactor expansion (note that solid filled data points at 0 h and 66 h were excluded from the model fit).

Figure 2:
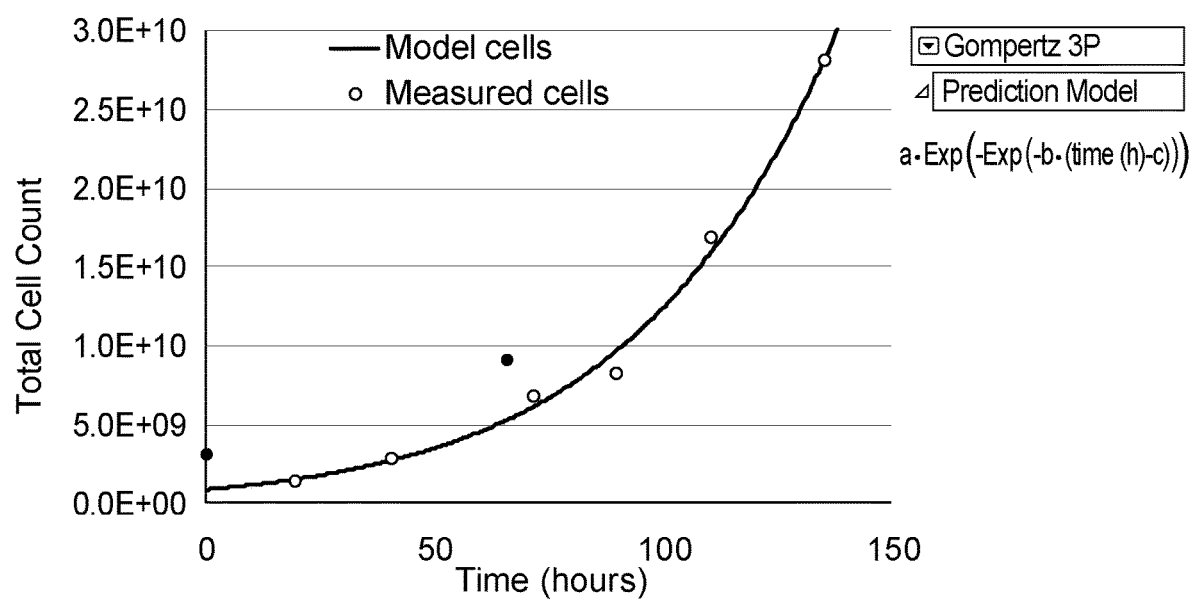
FIG. 2 depicts an example of a prediction model (right) and sample-based data with model fit (left) for cell count vs time in a 10 L pluripotent stem cell bioreactor expansion.
Figure 3:
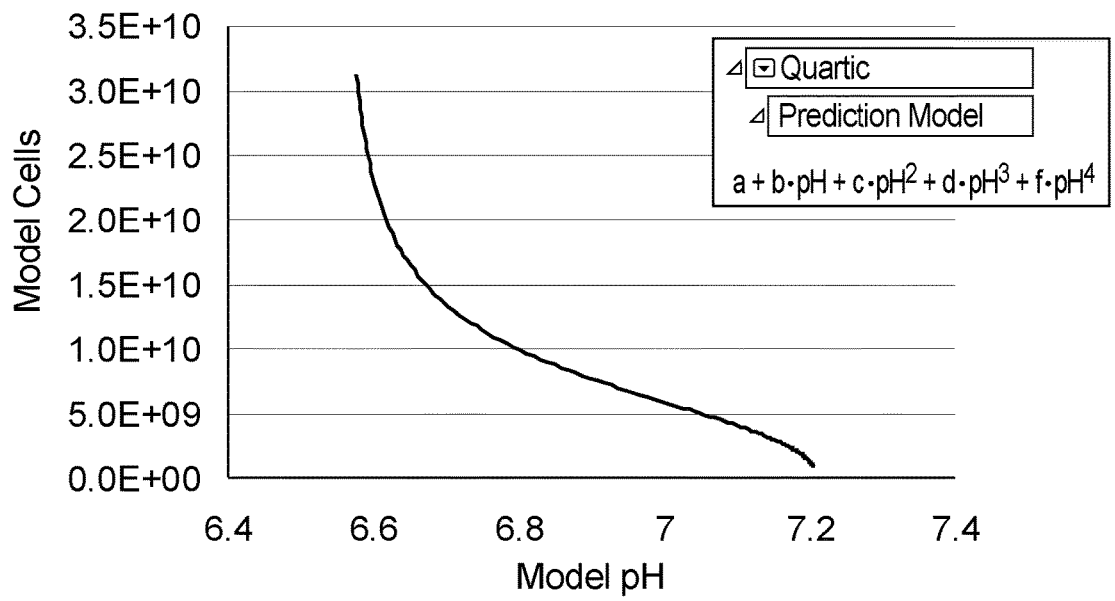
FIG. 3 depicts an example prediction model (right) and time-matched model fit (left)

To generate a predictive viable cell biomass correlation, data from FIG. 1 and FIG. 2 were time-matched and plotted against each other to yield the relationship shown in FIG. 3. This data was well described by a quartic model (r2=0.993), but the skilled person in the art would appreciate that there are many other models that could be used.

Figure 4:
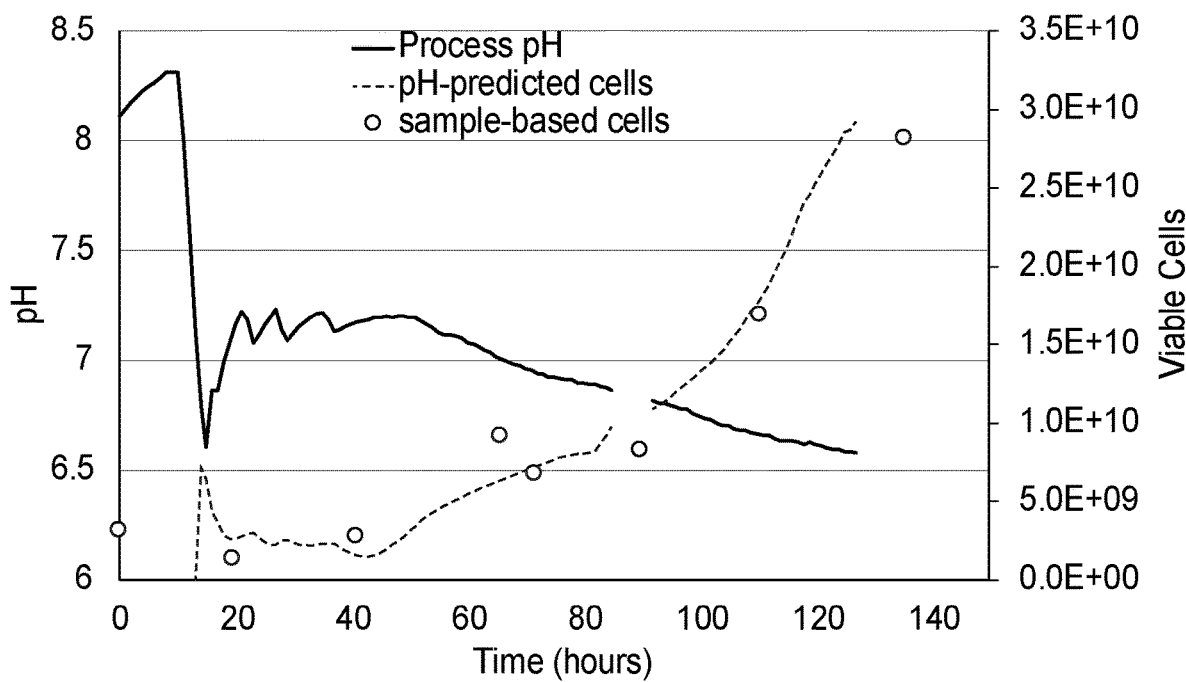
FIG. 4 depicts an example of continuous process pH data, sample-based cell counts, and cell mass prediction based on application of the equation shown in FIG. 3 to the continuous process pH data.

Using the relationships developed in FIGS. 1-3, the inventors found that the equation described in FIG. 3 could be used to predict or determine a close approximation of the viable cell density of the PSC bioreactor culture directly from the continuous process pH data. An example of such a prediction is illustrated in FIG. 4, which depicts example continuous process pH data (solid black line) and sample-based cell counts (circles). Applying the equation developed and shown in FIG. 3 to the continuous process pH data generates a cell mass prediction shown in FIG. 4 in stippled line.

The above mathematical descriptions were also applied for 1) dissolved oxygen when a run is not controlled (i.e. process value is allowed to drift down with dissolved oxygen consumption), 2) dissolved oxygen in a controlled run (i.e. dissolved oxygen is held constant and the increase in control value (CV or sensor "call" signal) is used for predictions), 3) oxygen gas flow from a mass flow controller, and 4) oxygen uptake rates (OUR) calculated from process data. The relationship demonstrated above for pH, combined with an example for dissolved oxygen, results in a bi-variate relationship that may be used to predict biomass in either a united multivariate equation, or in a parallel redundant manner. The importance of predicting from more than one continuous process variable is described.

Figure 5:
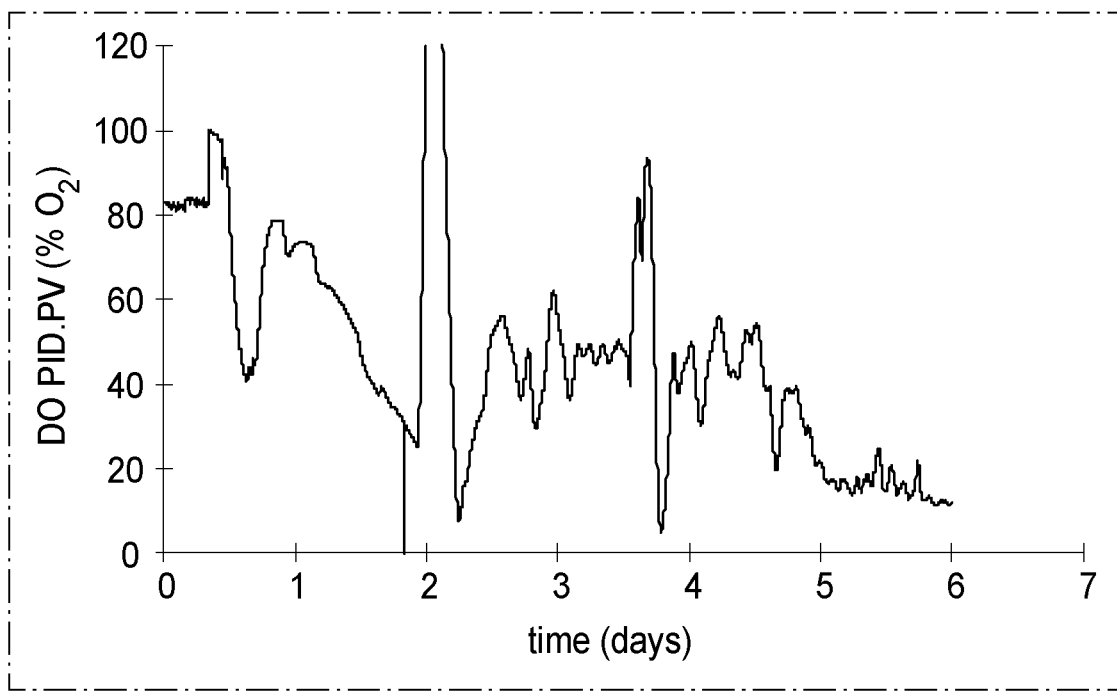
FIG. 5 depicts example continuous dissolved oxygen process data from process value (PV, top) and control value (CV, bottom)
Figure 5:
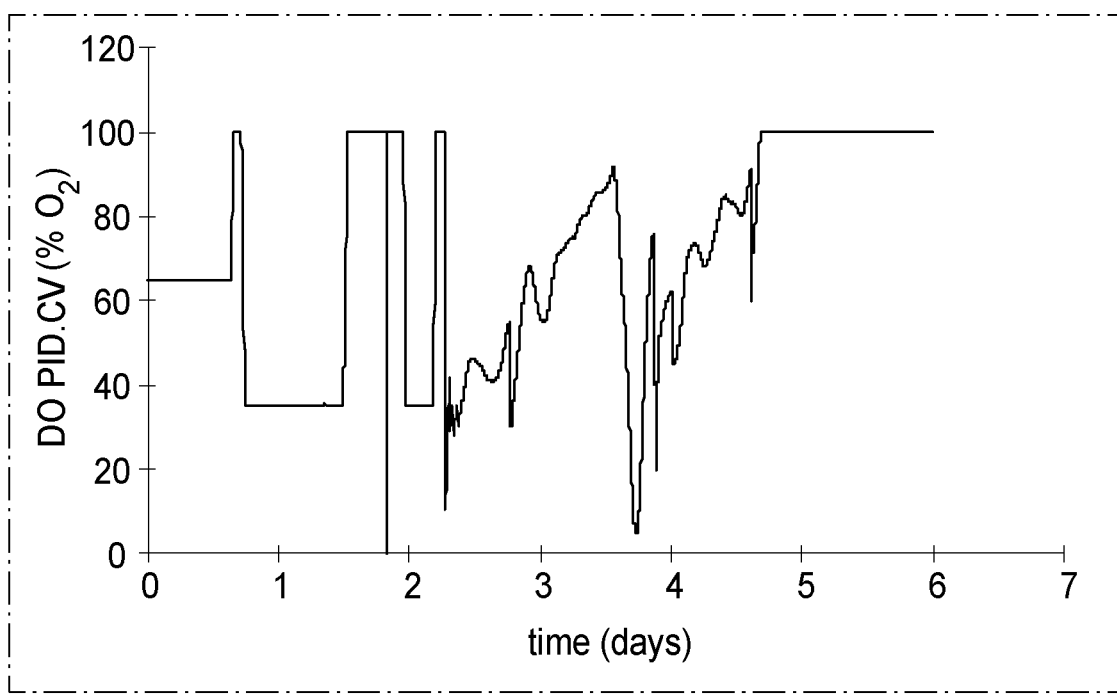

With reference to FIG. 5, in another example involving a 10 L PSC expansion, as an example of the advantage of using a multivariate predictive approach, the inventors examined the dissolved oxygen relationships in a 10 L vessel. In this example, PID (proportional, integral, derivative) feedback controllers were not set up for adequate control and the continuous process data was not amenable to the mathematical treatments above. The process value data (FIG. 5, top) was confounded by the switch between air supplied oxygen and pure oxygen provision (at ~2 days). However, the inventors observed that the control value data (FIG. 5, bottom) demonstrated an increasing trend which could be additionally leveraged into a multivariate cell prediction model.

Together, the above relationships, determined by the inventors, have allowed for the development of a sample-free scaled up seed train. In an embodiment, the predicted biomass values were used to decide when and how much to increase the rate of feed provided to the vessel or bioreactor and also to inform the decision to harvest the intermediate and final manufacturing stages (between 2-4e6 cells/mL).

Feeding Control

Figure 6:
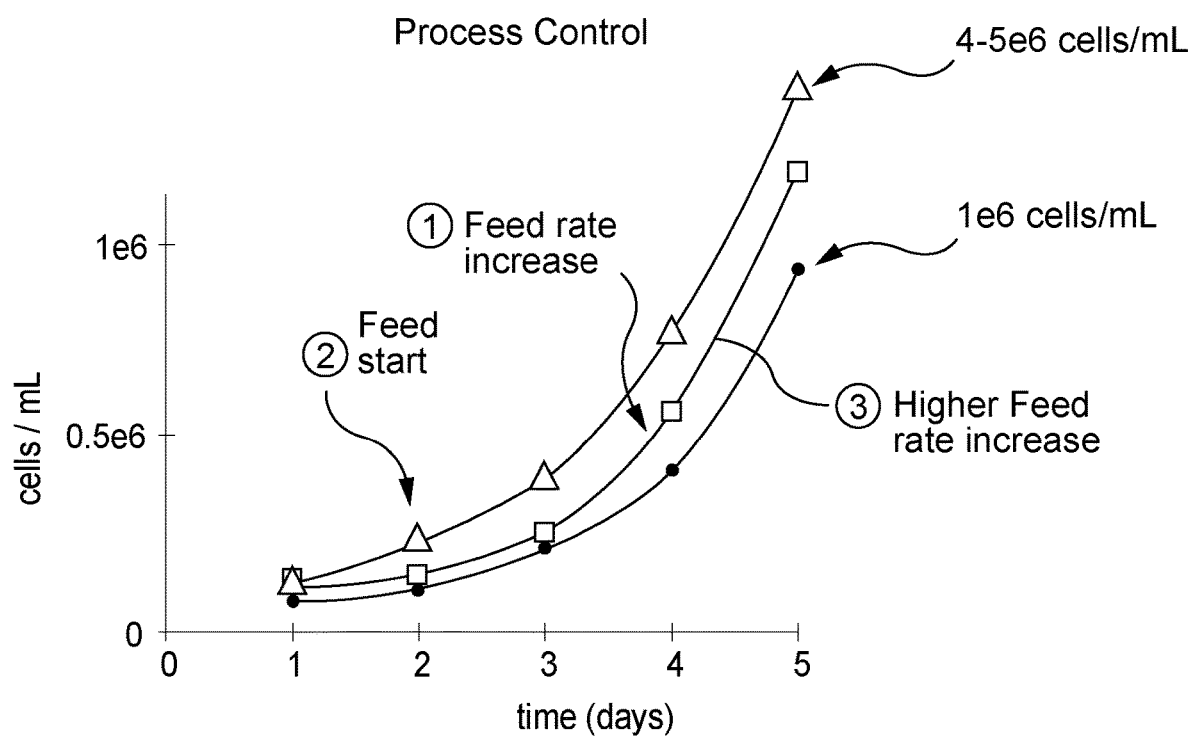
FIG. 6 depicts example data of feeding control enabled by biomass modeling.

FIG. 6 depicts example data of feeding control enabled by biomass modeling, and an improvement made to the existing manufacturing process that was enabled by the predictive biomass measurements described above. Originally, the process was fed at a low rate from day 2 (feed start 2 in FIG. 6). It was sampled daily and the cells would normally expand to a point requiring increased feed by day 4 (feed rate increase 1 in FIG. 6). This would yield a growth kinetic capable of producing approximately 1e6 cells/mL (lower plotted line). With the presently described predictive cell production feedback being based on real-time pH and DO sensor readings, for example, and thus being more frequent than the frequency at which physical samples could be taken, the inventors were able to increase feeding rates earlier using the presently described multivariate predictive cell production determination (middle plotted line) and more aggressively (top plotted line) drive the process to higher cell titre (4-5e6 cells/mL).

Autologous Example—T-Cell Manufacturing

Figure 7:
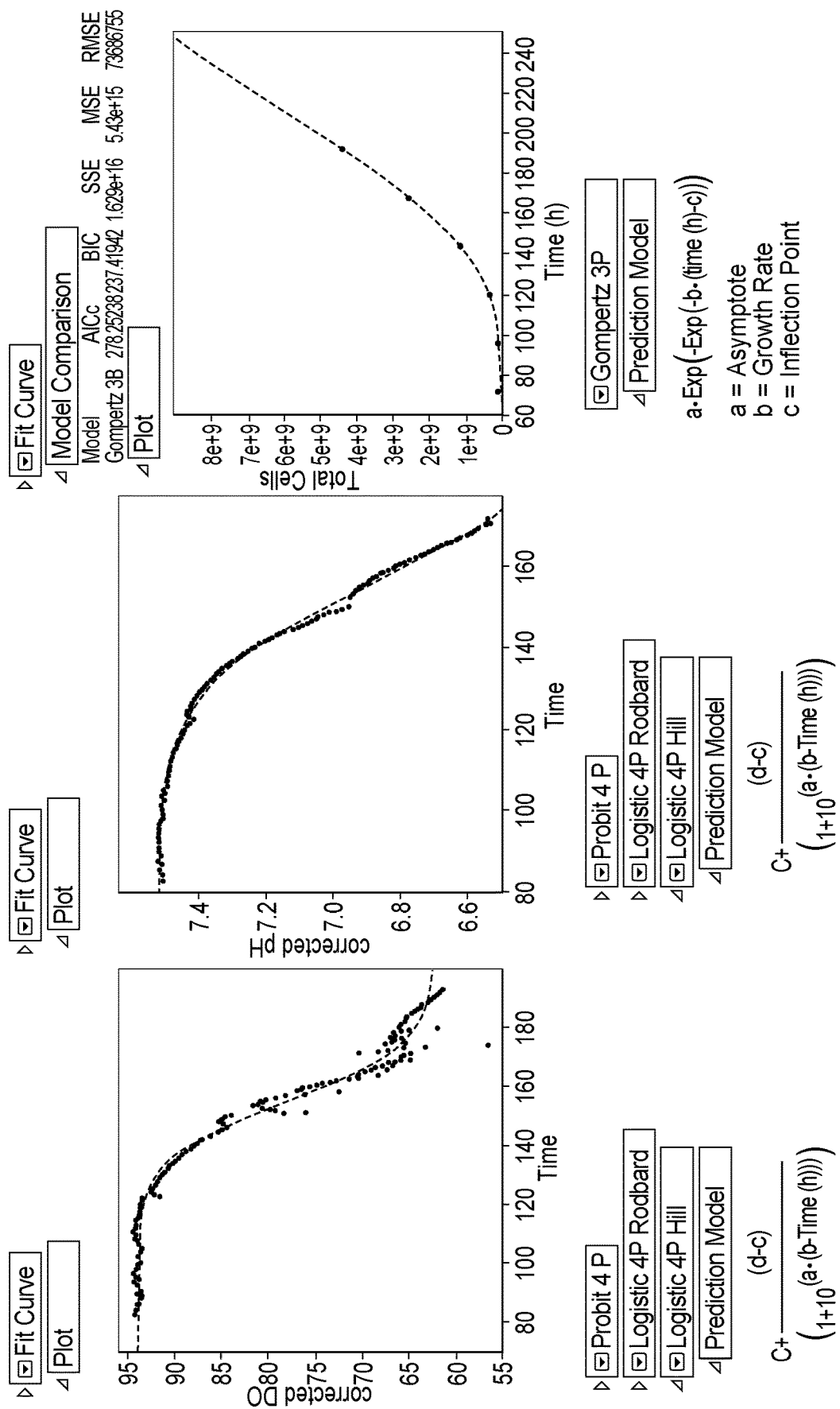
FIG. 7 depicts example model fits of continuous DO data (left), continuous pH data (middle) and sample-based cell counts (right)

A similar mathematical approach was applied to the manufacturing of an autologous T-cell product in a rocking bed bioreactor, demonstrating the cell type and platform agnostic character of the presently described approach. Continuous data (pH and DO) and sample based data (cell counts) were subjected to curve fitting as previously described, and as shown in FIG. 7, which depicts example model fits of continuous DO data (left), continuous pH data (middle) and sample-based cell counts (right). Two unique time-matched fits were generated for each of pH and DO versus cells (Excel-based polynomial and jmp derived logistic 4 parameter Hill), as well as a multivariate relationship including both pH and DO, and finally an average of all 5 fits.

Figure 8:
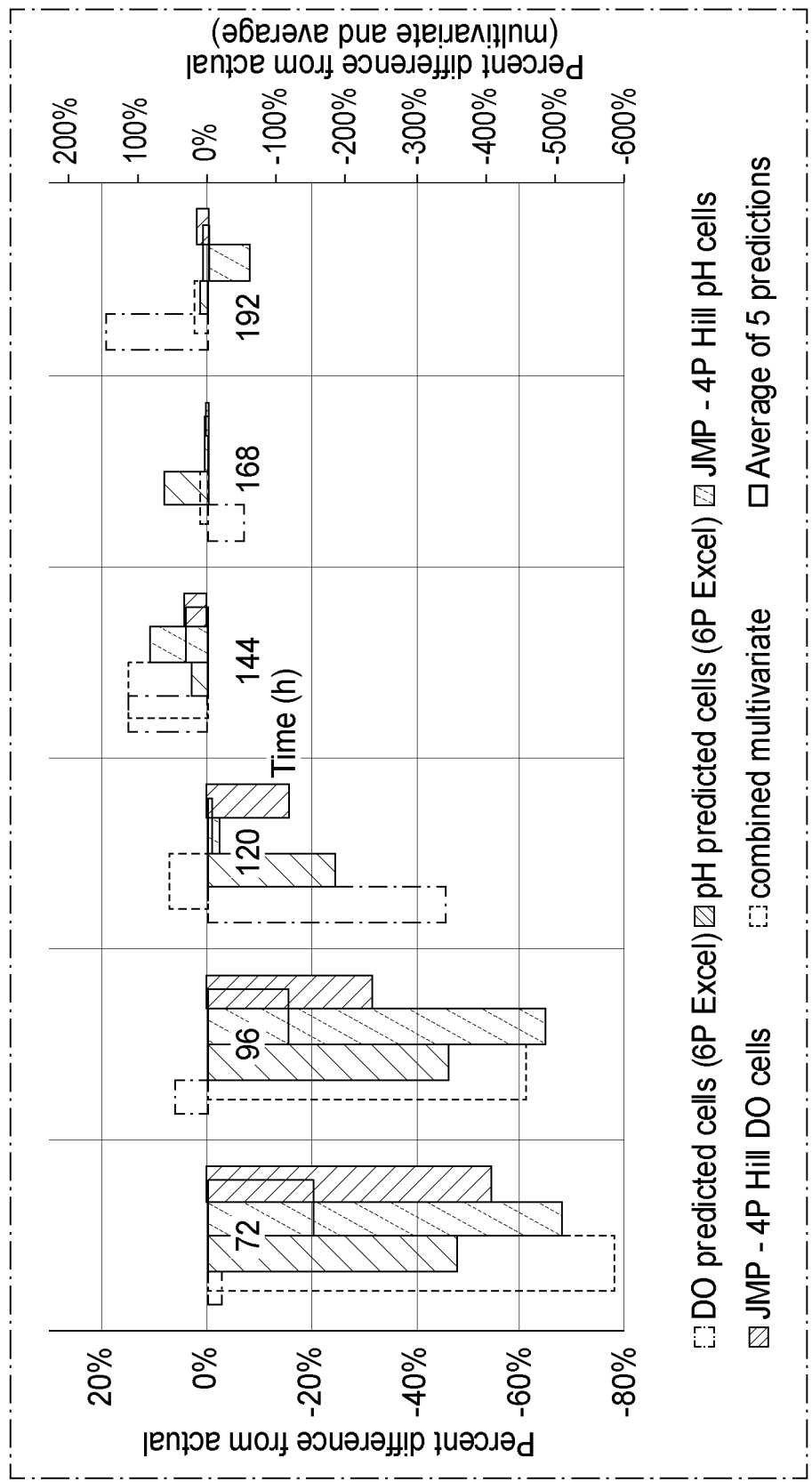
FIG. 8 depicts an example graph showing percent difference of multivariate cell mass predictions from actual measured values, with open series (combined multivariate and 5 prediction average) shown on the secondary axis.

As a demonstration of the utility of multivariate and parallel redundant predictive models, several series, shown in FIG. 8, show a common theme of increased error at early time points. This is understandable and attributable to the system as pH and DO changes are minimal early in cell expansion. However, as cell expansion proceeds and the dynamic range of pH and DO are traversed, the inventors have found that the ability to predict cell biomass production, based on the correlations between cell biomass production and pH/DO decrease, is increased. FIG. 8 also demonstrates that multiple parallel (i.e., the DO predicted cells, pH predicted cells, JMP—4P Hill pH cells, and JMP—4P Hill DO cells), multivariate and an average of all correlations represent a comparable and predictable mode of operation. Each section of the bar graph in FIG. 8 depicts 6 bars, as indicated in the legend in FIG. 8. Regarding the JMP-4P Hill pH cells bar shown at 168 hours, while it is difficult to make out, the data series is shown, with a value of 1%; because the percent difference from actual is quite low, it is covered in the graph by the "Average of 5 predictions" bar. FIG. 8 shows, and the inventors found, that as the prediction proceeds in time, the difference from actual decreases (i.e. the prediction accuracy increases), which demonstrated to the inventors the value of recursive fitting, as it adjusts in real-time to the data retrieved from the sensors.

As growth curves and kinetic data can be generated from continuous process data, the equations describing growth in FIGS. 2 and 7 can be recursively fit as real-time pH and DO sensor data is received. The equations in Table 1, below, can be updated in real-time (with operator input of start time (time zero or "T0" in Table 1) and target cell density) and displayed in a manufacturing graphical user interface (GUI), such as GUI 90 shown in FIG. 9, which depicts an example interface (a Xuri™ interface is depicted) including real-time updated countdown time to harvest 92 as well as a time-stamp 94 for harvest time. Of particular interest for manufacturers will be the "time to harvest" and "harvest time" to allow for process, operator and patient scheduling. In an embodiment, this could be displayed as shown in Table 1 and FIG. 9, or transmitted directly to cloud-based scheduling of people, downstream resources and logistics.

TABLE 1

Predictive analytics calculated from recursive growth curve fitting fed by real-time correlation to pH and DO (user input, for this embodiment, is shaded)

| T0 (mm/dd/yyyy hh:mm) | Mar. 13, 2018 9:00 | date/time |
|---|---|---|
| Target cell Density | 1.50E+10 | cells |
| Time to harvest (h) | 210.5 | h |
| Time to harvest (days) | 8.8 | days |
| Harvest Time | Mar. 22, 2018 3:30 | date/time |
| Predicted Cell Density at Harvest | 1.49E+10 | cells |
| $\mu$ (h$^{-1}$) | 0.0322 | h$^{-1}$ |
| doubling time (h) | 21.5 | h |

Described below are various further embodiments based on the demonstrated correlation-based predictions discussed above. The present description generally relates to methods and systems for electronic monitoring of two or more bioreactor sensor readings to determine or predict, in a non-invasive manner (i.e., in a manner that does not require the physical sampling or removal of aliquots of substrate from a bioreactor) cell biomass production in a bioreactor, based on predetermined (e.g., where a model system has been determined) or algorithmically recursively fit or adapted correlations between the sensor readings and cell biomass production, as shown above. Once the correlations are determined, an approximate cell biomass or bioreactor product amount may be predicted based on the observed sensor readings. The presently described embodiments employ two or more sensor readings, and the prediction may be based on either independent, parallel consideration of the multiple sensor readings (to reduce the risk of errors from fluctuation of a single sensor) or in a multivariate manner. In an embodiment, outliers in the sensor readings may be ignored in the predictive determination of cell biomass or bioreactor product production, as shown in FIG. 2.

In the various described embodiments, the methods and systems herein are expected to facilitate cell biomass prediction without the need for physical removal of aliquots of substrate from the bioreactor, which is expected to reduce or mitigate the risks and costs previously described herein. In various embodiments, the methods and systems herein are expected to facilitate monitoring and recording of bioreactor data and predicted cell biomass production, which tends to facilitate scheduling of "harvest time" which, in turn, facilitates process, operator and patient scheduling, as previously described. The determination of the approximate amount of the product may be performed 1) continuously by the processor in real-time upon A) receipt of the sensor data (whether the sensor data is received continuously or at discrete intervals), or B) on demand upon user input requesting the determination of a predicted approximate amount of product based on the sensor data received up to that point in time, or 2) at discrete time intervals (which may be preconfigured) by the processor based upon either continuous receipt of the sensor data, or receipt of the sensor data at discrete time intervals (which may or may not be preconfigured, or at the same intervals as configured for the processor to determine the approximate amount of the product) in which case a user request to determine a predicted approximate amount of product may be based on the most recently received sensor data. In either case, the system may poll for updated sensor data at the time of receipt of a user request for a determination of a predicted approximate amount of product. The presently described methods and systems may be used to predict or determine other possible outputs also, without the need for the physical removal or sampling of aliquots of substrate from the bioreactor, such as metabolite output or any other product of the bioreactor cell manufacturing process.

While the inventors have demonstrated, through cell biomass sampling and concurrent sensor readings of pH and DO, that there is a correlation between pH and DO decline and cell biomass incline, which the inventors have leveraged to predict or determine an approximate cell biomass production without invasive sampling, it will be appreciated that various other sensor readings of the bioreactor media substrate throughout the course of a cell therapy manufacturing run may be used to determine similar correlations. Example sensor readings that may be employed (i.e., different physical attributes that may be measured by the different sensor types) in the presently described embodiments include, but are not limited to, temperature, conductivity, NO/NOx, volatile organic compounds (VOCs), ozone, chlorine, reduction-oxidation (redox) potential, agitation, inward gas flow, outward gas flow, gas consumption, capacitance, optical density, particle size, metabolite concentration, pressure, cytokine or growth factor concentration, and vessel weight. It will further be appreciated that the presently described methods and systems may be employed with any type of bioreactor (including, but not limited to, batch, fed batch or perfusion/continuous stirred-tank reactors, and rocking bed reactors) for growing cells from cell cultures, based on any suitable medium or substrate (including liquid or solid media), and vessel types other than bioreactors (and as such, the use of the term "bioreactor" herein is meant to encompass all such bioreactors and vessels). Furthermore, while the inventors have demonstrated the applicability of the presently described methods and systems with pluripotent stem cell (PSC) and T cell biomass predictions, the methods and systems described herein may also be used to predict the production of, generally, immune cells, stem cells, stem cell-derived cells, and virus producing cells, as well as other types of cells (including Natural Killer cells (NKs), T-regulatory cells (T-regs), Tumor Infiltrating Lymphocytes (TILs), Mesenchymal Stem Cells (MSCs), and the like), and differentiated cells based on the pluripotent stem cells (i.e., PSC-derived cells) and viral vector or exosome producing cells.

In a further embodiment, recursive model fitting, which may take place in real-time or at discrete time intervals, may be utilized to link the process data from the plurality of sensor inputs to a predictive cell mass, metabolite output, process input (such as feeding) requirement, or other cascade control (or some combination thereof). In an aspect, the predicted cell biomass (or other predicted quantity, e.g., metabolite output) may be used as an input to a feedback controller for providing process input (e.g., feed) to the bioreactor in order to effect a desired growth trajectory for the cell biomass, as described in greater detail below. As used herein, "process input" includes any media additions, such as feed, gas flows (such as to maintain a certain pH level or to alter pH depending on cell density and growth rates, for example), dissolved oxygen (DO), specific substrate media components, or any other input that can be provided to the bioreactor (including, e.g., agitation of the bioreactor), and further includes any corresponding volume removal with cell retention (i.e., perfusion to remove impurities).

Figure 10:
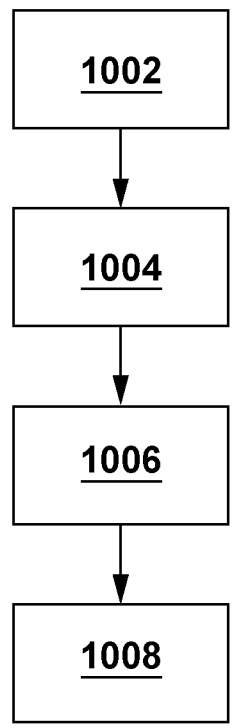
FIG. 10 depicts a flow diagram of an example embodiment of computer executable instructions described herein.
Figure 11:
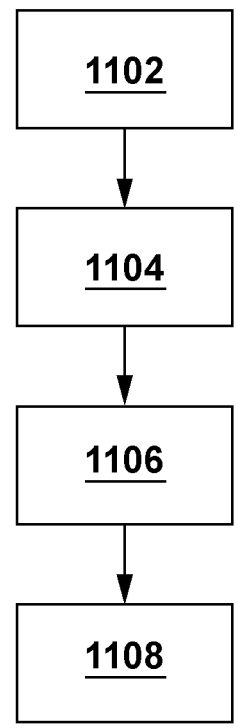
FIG. 11 depicts a flow diagram of another example embodiment of computer executable instructions described herein.

With reference to FIG. 10, in an embodiment, a computer-implemented method 1000 for approximating product production in a bioreactor comprises: providing 1002 a bioreactor containing live cells in a substrate, the bioreactor for cultivating, over a time period, a product derived from or of the cells (i.e., the cells themselves) during a manufacturing process (such as an autologous or allogeneic cell or gene therapy manufacturing process, or the manufacturing of viral vectors, for example); providing 1004 two or more sensors for measuring respective two or more different conditions or physical attributes (such as those described above) of the substrate or bioreactor contents during the time period of the manufacturing process; receiving 1006, at a processor, sensor data from the two or more sensors; and determining 1008 via the processor, upon receiving the sensor data (including in substantially real-time upon receiving the sensor data, or not in substantially real-time), based on an algorithm (predetermined as described herein based on a determined correlation model, or recursively fit or adapted to process data, which would not require a prior determination of a correlation model) that correlates the sensor data and the product production (such as described above), an approximate amount of the product. With reference to FIG. 11, in accordance with a further embodiment, a computer-implemented method 1100 for approximating product production in a bioreactor comprises: providing 1102 a bioreactor containing live cells in a substrate, the bioreactor for cultivating, over a time period, a product derived from or of the cells (i.e., the cells themselves) during a manufacturing process (such as an autologous or allogeneic cell or gene therapy manufacturing process, or the manufacturing of viral vectors, for example); providing 1104 two or more sensors for measuring respective two or more different conditions or physical attributes (such as those described above) of the substrate or bioreactor contents during the time period of the manufacturing process; receiving 1106, at a processor, sensor data from the two or more sensors; and determining 1108 via the processor, based on a recursively adapted or recursive algorithm (determined as described herein) that correlates the sensor data and the product production by independent consideration of the sensor data of the two or more different physical attributes or by multivariate consideration of the sensor data of the two or more different physical attributes, an approximate amount of the product. As described herein, the inventors have surprisingly discovered the ability to approximate bioreactor product production based on multiple sensor readings. In particular, this was demonstrated for cell therapy manufacturing processes in which the manufacturing process product comprised pluripotent stem cells or T cells.

In further described aspects of the presently described embodiments are methods and systems for determining a rate of feed supply to the bioreactor. With reference to FIG. 12, in an embodiment, method 1200 comprises: providing 1202 a target or desired product density or amount; determining 1204 the approximate amount of the product via the processor in accordance with the methods and systems described herein; determining 1206 if the determined approximate amount of the product is lower than is required to achieve the target product density or amount within the time period of the manufacturing process (or some other time period, which may be input by a user), and if so, determining 1208 the rate of feed supply to the bioreactor required to achieve the target product density or amount within the time period of the manufacturing process (or some other time period, which may be input by a user); and adjusting 1210 the rate of feed supply to the bioreactor to the determined rate of the feed supply. In yet further aspects of the presently described embodiments are methods and systems for determining a rate of supply of a process input to the bioreactor. With reference to FIG. 13, in an embodiment, method 1300 comprises: providing 1302 a target or desired product density or amount; determining 1304 the approximate amount of the product via the processor in accordance with the methods and systems described herein; comparing 1306, via the processor, the determined approximate amount of the product to the target product density or amount; determining 1308 via the processor, based on the comparing, the rate of supply of the process input to the bioreactor required to achieve the target product density within the time period of the manufacturing process (or some other time period, which may be input by a user); and adjusting 1310 the rate of supply of the process input to the bioreactor to the determined rate of supply of the process input. The adjusting may be to increase or decrease the rate of supply of the process input (which, as described herein, may also include an increase or decrease in the rate of removal of impurities or other materials from the bioreactor while retaining cell mass such as by perfusion). The adjusting may be the result of a determination, based on the comparison 1306 of the determined approximate product amount to the target product density or amount, that the determined approximate product amount is below, at, or above the target product density or amount. In further embodiments, the methods and systems described herein may be used to determine approximate amounts of any process metric related to the bioreactor manufacturing process, and not just an approximate product amount. In yet further embodiments, the methods and systems described herein can be used to determine rates of supply of process inputs to the bioreactor based on comparisons to targets of any such process metrics, and not just a target product density or amount.

The above described methods may be based on the real-time monitoring and processing of multiple bioreactor sensor readings in order to determine, in real-time, predicted cell biomass production, or may be based on the monitoring of multiple bioreactor sensor readings at discrete time intervals (which may be preconfigured), or on demand based on user input. It will be appreciated that in order to determine or predict an approximate amount of product, such as cell biomass, substantially in real-time upon user request (or upon receipt (at discrete intervals or continuously) of sensor data, although in certain embodiments, the determination or prediction of an approximate amount of product may not be performed in real-time upon receipt of sensor data), the above described methods are required to be computer-implemented. As used herein, the term "real-time" includes "substantially real-time", to account for lags in computer processing, digital read/write operations, and communications transmissions, as would be known to the skilled person in the art. In an embodiment, a system 1400 for carrying out the presently described methods may comprise a bioreactor 1402, including two or more sensors 1404 (such as for reading pH and DO of the media substrate), a feed input port 1406, and a waste output port 1408, among other inputs and outputs known in the art. The bioreactor may include an onboard processor or controller 1410 for reading the sensor data and, based on a predetermined or recursively modeled correlation, determining the predicted cell biomass or amount of produced product. Additionally or alternatively, a separate computing device 1450, with processor 1452 (described further below), may be used for this purpose. Processor 1410 and/or 1452 (collectively, "a processor" or "the processor" herein) may make the determination in real-time (or not in real-time), and recursively based on continuous inputs from the sensors. In a further embodiment, the bioreactor may include a (or there may be a separate) feedback controller 1412 communicatively coupled to the processor and to one or more feed input ports (or output port(s)) of the bioreactor, and which causes feed to be provided to (or substance to be removed from) the bioreactor based on the predicted cell biomass or other determined prediction(s), and said feedback controller may receive and provide feedback control of bioreactor input(s) (or output(s)) based on real-time (or not real-time) predictions of cell biomass or other determined prediction(s). In yet further embodiments, the processor and feedback controller/processor may be housed in the same physical unit, or may comprise the same unit. In yet other embodiments, any controllers or processors utilized for the described methods and systems may be remotely located from the bioreactor. Communications between the controllers and bioreactor may be via wired or wireless connection, using transmitters, receivers, and/or transceivers. Further aspects of systems for carrying out the methods herein are described below.

Figure 14:
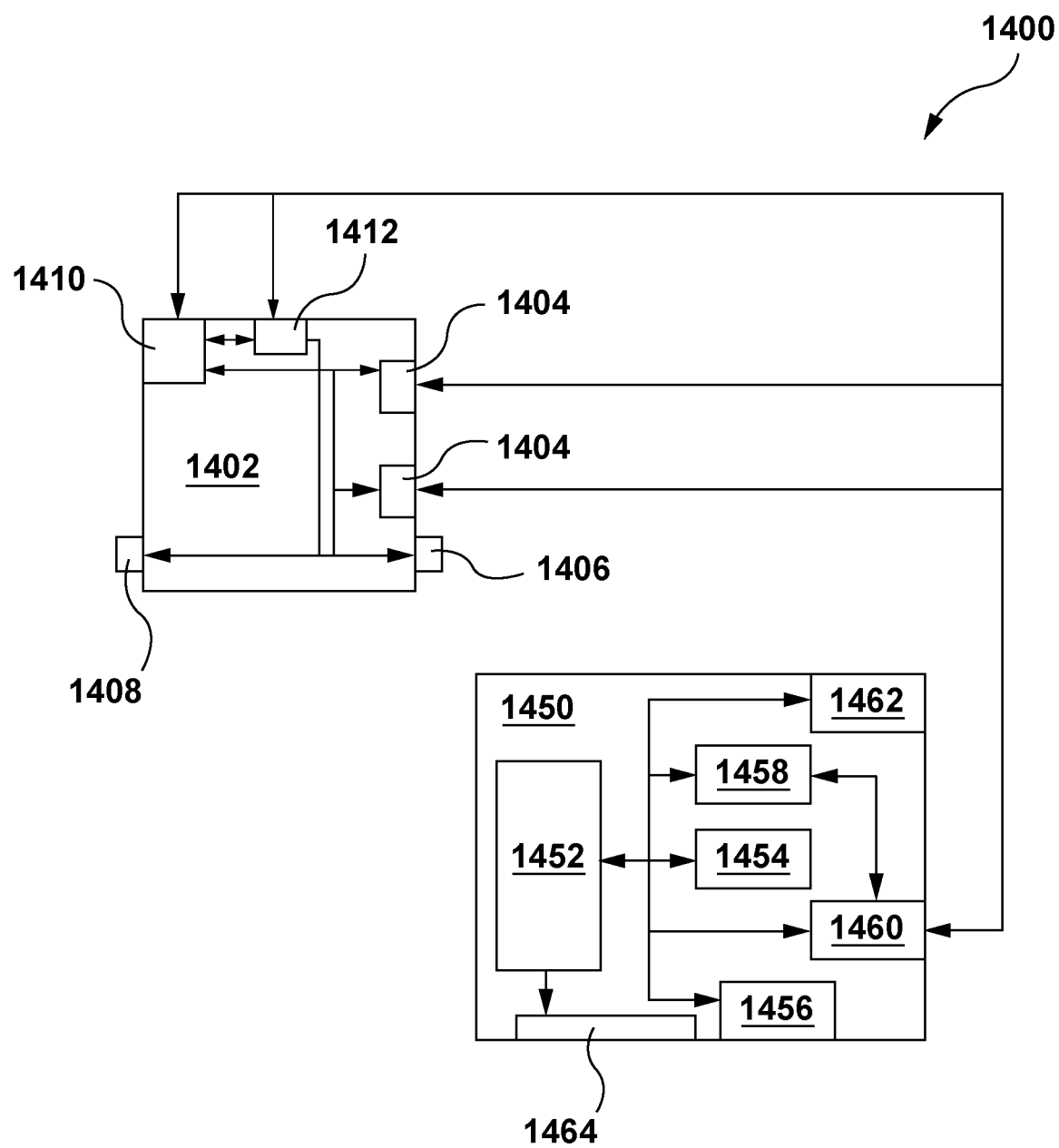
FIG. 14 depicts a schematic diagram of an example embodiment of a system described herein.

Referring to FIG. 14, in addition to the bioreactors and sensors described herein, system 1400 for carrying out the presently described methods may further comprise a computing device 1450 comprising a processor 1452, a memory 1454, an input device 1456, and a communication module 1458. The computing device may further comprise receivers, transmitters and/or transceivers 1460. The processor may be communicatively coupled to the memory, the input device, the communication module, and/or any receivers, transmitters and/or transceivers, and as described herein, the computing device may be remotely located from or co-located with the bioreactor, and communicatively coupled to the sensors. All processors described herein may be configured to carry out any or all method steps suitable for computer implementation. For example, in an embodiment, the processor may be configured to: receive 1006, 1106 (e.g., via a receiver 1460 or the communication module 1458) sensor data from the two or more sensors 1404; and determine 1008, 1108, based on a predetermined or recursively adapted or recursive algorithm stored in the memory 1454 that correlates the sensor data of two or more different physical attributes or conditions (such as those described above) and product production by independent consideration of the sensor data of the two or more different physical attributes or by multivariate consideration of the sensor data of the two or more different physical attributes, an approximate amount of the product.

In embodiments involving the determining 1208, 1308 and/or adjustment 1210, 1310 of the rate of process input (e.g. feed) supply to the bioreactor, system 1400 may further comprise feedback controller 1412 for carrying out the adjustment of the rate of the process input (e.g., feed) supply, as discussed above. The feedback controller may be communicatively coupled to the computing device 1450 and the bioreactor 1402, such as to a feed input port(s) 1406 (or output port(s) 1408) of the bioreactor. Upon receipt from the communication module 1458 of the computing device 1450 of the determined adjusted rate of process input (e.g., feed) supply, as determined by the processor in accordance with methods described herein, the feedback controller 1412 may adjust the rate of the supply of the process input (e.g. feed) to the bioreactor to the rate of supply of the process input (e.g., feed) determined by the processor, such as by opening, closing, or otherwise adjusting the rate of flow of the process input (e.g. feed) through the input 1406 or output 1408 port(s) of the bioreactor.

The processor 1410 and/or 1452 of the described system 1400, for processing information associated with the process(es) or method(s) described herein, may be, for example, any computer processor known in the art capable of performing calculations and directing functions for interpreting and/or performing input, output, calculation, and display of data in accordance with the disclosed methods. The processor may comprise any type of processing unit, such as typical computer processor(s), controller(s), microcontroller(s), microprocessor(s), and/or programmable logic controllers (PLCs). The information to be processed by the processor may include, for example, information contained in analog or digital signals and/or translated signals and/or information contained in a data storage. Processing of the information may involve, for example, performing calculations on received signals such as, but not limited to, vector analysis, picture identification, pattern recognition, frequency analysis/Fourier transforms, numerical computations, machine learning, or, as described herein, applying predetermined or recursively fit correlative algorithms to received sensor data. In some embodiments, the system comprises more than one processor, and reference herein to "processor" includes reference to multiple processors, and vice versa.

In an embodiment, the processor 1410 and/or 1452 is in communication with the two or more sensors 1404 of the bioreactor 1402. In another embodiment, the processor 1410 and/or 1452 may also be in communication with data storage(s) 1462, and optionally, display(s) 1464 (such as for displaying GUI 90). The components of the system 1400, such as the bioreactor 1402, sensors 1404, computing device(s) 1450, processor(s) 1410 and/or 1452, feedback controller(s) 1412, data storage(s) 1462, and/or display(s) 1464, and any other components of system 1400, bioreactor 1402 or computing device 1450, may communicate using any electronic wired or wireless means or protocols for communication known in the art, including but not limited to Ethernet™, Bluetooth™, WiFi™, infrared, near-field communications (NFC), radio-frequency identification (RFD), WiMAX™ (fixed or mobile), cellular communications protocols such as GSM, EDGE, GPRS, CDMA, UMTS, LTE, LTE-A, IMS, and any other cellular communications protocols including, but not limited to, up to and including 5G protocols as established under the 3GPP, for example, and any other communications protocols suitable for the method(s) and system(s) described herein, including any proprietary protocols. Components of the system may exist on the same network or on separate networks, and the network(s) may include any type of network suitable for the system(s) and method(s) described herein, including but not limited to wired or wireless personal area networks (PANs), local area networks (LANs), mesh or ad hoc networks, wide area networks (WANs), metropolitan area networks (MANs), virtual private networks (VPNs), and any other suitable network type, as well as any suitable network configuration or topology (e.g., token ring, star, bus, mesh, tree, etc.). The presently described system(s) further includes any components necessary to effect the communication and/or network type employed, such as wireless or wired routers and access points.

The presently described methods and systems may be implemented on a secure network to which access may be limited to authorized users by any known means, and which may be protected by known security measures, such as by use of firewalls. In some embodiments, authentication may be required before granting access to authorized users, such as where autologous cell manufacturing and/or patient data is involved, and/or where compliance with government regulations is mandated (such as Title 21 of the U.S. Code of Federal Regulations). Such authentication may be implemented for any one or more of the system components, such as for access to a computing device or machine housing the processor, access to data storage, access to a database of the data storage, access to any of the sensors or sensor readings of the bioreactor, access to a graphical user interface (GUI) of the system, access to the bioreactor, etc. Security of the presently described methods and systems may be further provided for by encrypting communications among system components by any means or protocols known to persons skilled in the art, such as Internet Protocol Security (IPSec), Transport Layer Security (TLS), Secure Sockets Layer (SSL), etc., in order to reduce the potential for the tampering with or corruption of the preprogrammed correlative algorithm(s), for example.

The presently described system may also include a data storage 1462 for storing information associated with the described methods. The data storage may include, for example, various types of local (as shown in FIG. 14) or remote memory devices such as a hard disk or hard drive (of any type, including electromechanical magnetic disks and solid-state disks), a memory chip, including, e.g., random-access memory (RAM) and/or read-only memory (ROM), flash memory, optical memory such as CD(s) and DVD(s), floppy disks, and any other form of optical, physical, electronic, and/or magnetic memory devices in or on which information may be stored. The data storage may comprise non-volatile memory. In some embodiments, the data storage may only be accessed via secure data transfer, which may be accomplished using one or more known server platforms and security protocols. The information to be stored in the data storage may comprise, for example, one or more predetermined algorithms for correlating sensor inputs to various outputs, such as cell biomass production, and records of such predicted determinations along with associated actions (such as feedings) and/or associated timestamps, unique identifiers, authorized users and associated authentication information for use in authenticating users for authorized access to the data storage or any other system component, and any other pertinent information. In operation, the data storage is in communication with the processor.

Figure 9:
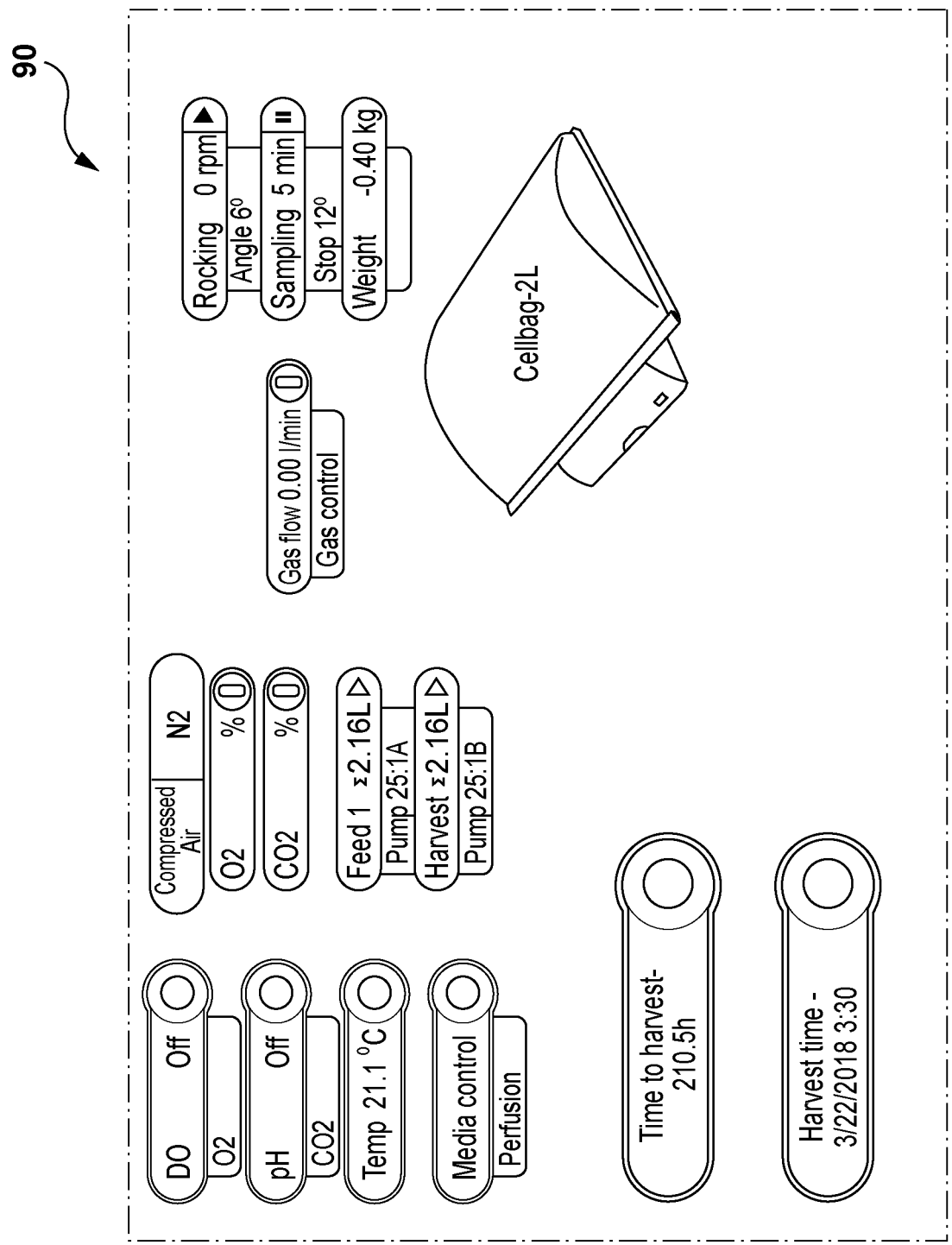
FIG. 9 depicts an example interface in accordance with an example embodiment.

The system may also include a display 1464 (which may be co-located with the processor as shown in FIG. 14, e.g. where the processor and display are part of a computer or server used for carrying out the method steps described herein) for visually presenting information associated with the described methods. The display may comprise, for example, a computer monitor (e.g., LCD, a CRT monitor, a projection (e.g., heads-up display (HUD) laser), etc. In some embodiments, the visual display may comprise, for example, that of a mobile device such as a tablet computer, cellular phone, smartphone, personal digital assistant (PDA), personal computer (PC), laptop computer, augmented reality display (e.g., Google™ Glass™ or Microsoft™ HoloLens™), etc. The information presented on the display may be as shown in FIG. 9, for example, and/or may include any other information collected in the course of carrying out the methods described herein, prompts for information entry associated with one or more steps of the described methods, and/or any predetermined formulae or algorithms, as previously described. The display may also be capable of receiving input (such as, e.g., where the display includes a touch-screen and is capable of receiving touch input and accordingly transmitting information to the processor).

It will be appreciated that components of the described system, such as a computer or machine housing the processor(s), include components known in the art that are required for their operation, such as a power supply, a network interface (such as a network interface card), network connectivity components (e.g., a modem, Ethernet cards, USB interface cards, FDDI cards, WLAN cards, etc.), a receiver, a transmitter, local memory, e.g. RAM, ROM, flash memory, cache or buffer memory, and/or other types of memory as previously described, a processing unit which may be in communication with input/output (I/O) devices, and all required circuitry, including bus(es). The bioreactor sensors 1404 may also include components specific to the sensor type, as would be known to the skilled person in the art. A computing device 1450, such as a computer or machine, housing the processor(s) may also include, for example, memory (e.g., hard disk storage, RAM, ROM, flash memory, cache or buffer memory, and/or other types of memory as previously described), attached input device(s) (e.g., a mouse, keyboard, microphone, etc.), attached output device(s) (e.g., a display monitor), and local memory for the processor(s) (e.g., registers, cached RAM, such as L1 cache, L2 cache, etc.). Depending on the system component, other components may also be present (e.g., a device in communication with a cellular network may include an antenna, etc.), and it will be appreciated that such components would be known to the skilled person in the art.

The described systems may comprise one or more redundant sensors for each of the two or more sensor types in the bioreactor, to provide further data for determining the correlation and thus to further improve predictive accuracy of cell biomass production based on the sensor readings (i.e., while each of the two or more sensor types in the presently described methods and systems are different types of sensors, each different type of sensor may have associated redundant sensors of the same type). Redundant sensor(s) for each of the two or more sensor types in the bioreactor may also be used in larger bioreactors to ensure the system is homogenous. Where, e.g., the sensor information is consistent among the redundant sensors, it may be stored in the data storage (e.g., in a database thereof), and where the information captured is not consistent among the redundant sensors, the respective sensor readings may be averaged or ignored altogether, or one of the redundant sensor readings, if not generally in line with the trajectory of the other received sensor data, may be discarded as an outlier, as previously described. Redundancy of the data storage and/or a database thereof is expected to help ensure the persistence of stored data and reduce the risk of data loss.

In some embodiments, the method(s) provided herein may be implemented using computer readable and executable instructions, as described above, for example. Accordingly, another aspect provided herein is a tangible, non-transitory computer-readable medium (i.e., a medium which does not comprise only a transitory propagating signal per se), such as memory 1454, comprising or having stored thereon or therein computer-executable instructions associated with the method(s) described herein, such as a local or remote hard disk or hard drive (of any type, including electromechanical magnetic disks and solid-state disks), a memory chip, including, e.g., random-access memory (RAM) and/or read-only memory (ROM), cache(s), buffer(s), flash memory, optical memory such as CD(s) and DVD(s), floppy disks, and any other form of storage medium in or on which information may be stored in a volatile or non-volatile manner, for any duration, included permanently or for brief instances. Such computer-executable instructions, if executed by a processor (e.g., of a computing device 1450, such as a computer housing the processor(s) described herein), cause the processor(s), and/or the computing device, computer or machine, to perform any of the method steps described herein that are suitable for computer implementation. Different implementations of the disclosed method(s) may involve performing some or all the steps described herein in different orders or some or all of the steps substantially in parallel. The functions or method steps may be implemented in a variety of programming languages, and such code or computer readable or executable instructions may be stored or adapted for storage in one or more machine-readable media, such as described above, which may be accessed by a processor-based system to execute the stored code or computer readable or executable instructions.

It will be appreciated that any method step, module, component, or system described herein that is suitable for computer implementation or required to be computer-implemented so as to effect real-time or substantially real-time execution may be implemented using computer readable/executable instructions or operations that may be stored or otherwise held by computer-readable media, as described herein.

Although reference has been made herein to certain specific embodiments, various modifications thereof will be apparent to those skilled in the art without departing from the purpose and scope of the invention as outlined in the claims appended hereto. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference as if set forth in their entirety.

The invention claimed is:

1. A system for approximating product production in a bioreactor, the system comprising:
   a bioreactor for cultivating, over a time period, a product derived from or of live cells in a substrate during a manufacturing process;
   two or more sensors for measuring respective two or more different physical attributes of the substrate during the time period;
   a computing device communicatively coupled to the two or more sensors, the computing device comprising
      a processor;
      a memory; and
      a communication module;
   the processor communicatively coupled to the memory and the communication module;
   the processor configured to
      receive, from the communication module, continuous sensor data from the two or more sensors;
      generate, in real-time, a recursive algorithm based on the continuous sensor data that correlates the continuous sensor data and the product production by independent consideration of the continuous sensor data of the two or more different physical attributes or by multivariate consideration of the continuous sensor data of the two or more different physical attributes; and
      determine, based on the recursive algorithm, an approximate amount of the product.

2. The system of claim 1 wherein the product comprises immune cells, stem cells, stem cell-derived cells, virus producing cells, natural killer cells (NKs), T-regulatory cells (T-regs), T cells, tumor infiltrating lymphocytes (TILs), mesenchymal stem cells (MSCs), pluripotent stem cells (PSCs), PSC-derived cells, viral vector producing cells, or exosome producing cells.

3. The system of claim 1 wherein the product comprises pluripotent stem cells (PSCs), PSC-derived cells or T cells.

4. The system of claim 1 wherein the two or more different physical attributes comprise temperature, conductivity, NO/NOx, volatile organic compounds (VOCs), ozone, chlorine, reduction-oxidation (redox) potential, agitation, inward gas flow, outward gas flow, pressure, vessel weight, pH, metabolite concentrations, cytokine or growth factor concentrations, capacitance, optical density, or dissolved oxygen (DO).

5. The system of claim 4 wherein a first of the two or more sensors comprises a sensor configured to measure said pH, and a second of the two or more sensors comprises a sensor configured to measure said dissolved oxygen (DO).

6. The system of claim 1 wherein the processor is configured to ignore outliers in the continuous sensor data in the determination of the approximate amount of the product.

7. The system of claim 1, further comprising:
   a feedback controller communicatively coupled to the computing device and the bioreactor, the feedback controller being communicatively coupled to the bioreactor by an input port of the bioreactor;
wherein the processor is further configured to determine a rate of supply of a process input to the bioreactor by:

comparing the approximate amount of the product to a target product density;

determining, based on the comparison, the rate of supply of the process input to the bioreactor required to achieve the target product density within the time period; and communicating to the feedback controller, via the communication module, an adjusted rate of supply of the process input to the bioreactor;

wherein, upon receipt, from the communication module of the computing device, of the adjusted rate of supply of the process input, the feedback controller adjusts the rate of supply of the process input to the bioreactor via the input port to the rate of supply of the process input determined by the processor.

8. The system of claim 1, wherein the bioreactor comprises one of a batch, a fed batch, a perfusion reactor, a continuous stirred-tank reactor, or a rocking bed reactor.

9. The system of claim 7, wherein the adjusted rate of supply of the process input is determined based on the comparison identifying that the approximate amount of the product is below, at, or above the target product density or amount.

10. The system of claim 9, wherein the process input comprises at least one selected from the group of: a media addition to the bioreactor, and a volume removal.

11. The system of claim 9, wherein the media addition to the bioreactor comprises at least one selected from the group of: a feed addition, a gas flow volume, a dissolved oxygen (DO) volume, and a specific substrate media component.

12. The system of claim 1, further comprising:
a display device in communication with the processor, the display configured to provide a representation of information related to the manufacturing process to a user.

13. The system of claim 11, further comprising:
a user input device in communication with the display and the processor, the user input device transmitting a user selection signal to the processor, the user selection signal based on a user selection from the user; and the processor further configured to receive the user selection from the user input device.

* * * * *